United States Patent
Wang

(10) Patent No.: US 11,490,944 B2
(45) Date of Patent: Nov. 8, 2022

(54) SYSTEM AND METHOD TO MAP ACTIVE RF CHANNELS TO RESPECTIVE PUMP HEADS FOR COOLED RADIOFREQUENCY ABLATION

(71) Applicant: Avent, Inc., Alpharetta, GA (US)

(72) Inventor: Ruoya Wang, Decatur, GA (US)

(73) Assignee: Avent, Inc., Alpharetta, GA (US)

( * ) Notice: Subject to any disclaimer, the term of this patent is extended or adjusted under 35 U.S.C. 154(b) by 366 days.

(21) Appl. No.: 16/538,876

(22) Filed: Aug. 13, 2019

(65) Prior Publication Data
US 2021/0045792 A1    Feb. 18, 2021

(51) Int. Cl.
*A61B 18/12*       (2006.01)
*A61B 18/02*       (2006.01)
(Continued)

(52) U.S. Cl.
CPC .............. *A61B 18/02* (2013.01); *A61B 18/12* (2013.01); *A61B 18/14* (2013.01);
(Continued)

(58) Field of Classification Search
CPC ...... A61B 18/1206; A61B 2018/00577; A61B 2018/00744; A61B 2018/00821
See application file for complete search history.

(56) References Cited

U.S. PATENT DOCUMENTS 5,334,181 A    8/1994  Rubinsky et al.
6,120,520 A *  9/2000  Saadat ............... A61B 18/1492
                                              606/159
(Continued)

FOREIGN PATENT DOCUMENTS

EP    2942023        11/2015
EP    2 977 021 A1    1/2016
(Continued)

OTHER PUBLICATIONS

International Search Report and Written Opinion dated Nov. 12, 2020, from International Application No. PCT/US2020/044953, 12 pages.

*Primary Examiner* — Daniel W Fowler
(74) *Attorney, Agent, or Firm* — Meunier Carlin & Curfman LLC

(57) ABSTRACT

A cooled radiofrequency ablation system and method are provided. In particular, a method to map active radiofrequency channels to respective pump assemblies for cooled radiofrequency ablation is provided. The system includes a pump system having a plurality of pump assemblies, a radiofrequency generator unit, and a plurality of cooled radiofrequency probes, wherein each cooled radiofrequency probe comprises a cable-tubing assembly having a radiofrequency cable connected to the radiofrequency generator unit and fluid tubing in communication with a pump assembly and connected to a cooling fluid source. Each pump assembly of the plurality of pump assemblies is activated individually in sequence. The system and method map each cooled radiofrequency probe to a respective pump assembly connected thereto by measuring a temperature drop delay time at the tip of each probe. The system and method can further detect the presence of multiple probes daisy-chained to a single pump assembly.

19 Claims, 7 Drawing Sheets

(51) Int. Cl.
*A61B 18/14* (2006.01)
*A61B 18/00* (2006.01)

(52) U.S. Cl.
CPC ............ *A61B 2018/00011* (2013.01); *A61B 2018/00583* (2013.01); *A61B 2018/00714* (2013.01); *A61B 2018/00744* (2013.01); *A61B 2018/00821* (2013.01); *A61B 2018/0231* (2013.01)

(56) References Cited

U.S. PATENT DOCUMENTS

| | | | |
|---|---|---|---|
| 7,004,961 B2 | 2/2006 | Wong et al. | |
| 7,344,499 B1 | 3/2008 | Prausnitz et al. | |
| 7,771,420 B2 | 8/2010 | Butty et al. | |
| 7,857,756 B2 | 12/2010 | Warren et al. | |
| 8,361,063 B2 | 1/2013 | Godara | |
| 9,072,540 B2 | 7/2015 | Jarnagin et al. | |
| 9,480,528 B2 | 11/2016 | Turovskiy et al. | |
| 9,603,990 B2 | 3/2017 | Woolford | |
| 9,662,169 B2 | 5/2017 | Schultz et al. | |
| 9,956,032 B1 | 5/2018 | Cosman et al. | |
| 2003/0199794 A1 | 10/2003 | Sakurai et al. | |
| 2005/0096549 A1 | 5/2005 | Gerber et al. | |
| 2005/0278007 A1 | 12/2005 | Godara | |
| 2007/0118191 A1* | 5/2007 | Godara | A61B 18/14 607/96 |
| 2013/0006232 A1* | 1/2013 | Pellegrino | A61B 18/12 606/33 |
| 2013/0030426 A1 | 1/2013 | Gallardo et al. | |

FOREIGN PATENT DOCUMENTS

| | | |
|---|---|---|
| WO | WO 03/000316 A1 | 1/2003 |
| WO | WO 2010/018569 A1 | 2/2010 |
| WO | WO 2017/039570 A1 | 3/2017 |

* cited by examiner

SYSTEM AND METHOD TO MAP ACTIVE RF CHANNELS TO RESPECTIVE PUMP HEADS FOR COOLED RADIOFREQUENCY ABLATION

FIELD OF THE INVENTION

The subject matter of the present invention relates generally to a system and method for mapping radiofrequency channels to cooling fluid pump assemblies to prepare for administering a cooled radiofrequency ablation treatment.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues with respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the electrode-tissue interface. By cooling the probe, the tissue temperature near the probe is moderately controlled. In turn, more power can be applied to the target tissue without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion.

Existing cooled radiofrequency ablation systems circulate cooled fluid in a closed loop flow path by a peristaltic pump or pumps. For example, the cooled radiofrequency ablation pump system 1 of the prior art, illustrated in FIG. 1, implements two pumps 2 that can be used to apply coolant fluid, supplied by an attached burette (not shown), to up to four cooled RF ablation probes controlled by a single generator (not shown). However, if more than two probes are used with the prior art pump system 1 of FIG. 1, the coolant lines of the additional probe(s) must be connected in series ("daisy-chained") to the first or second probe. In this configuration, the daisy-chained probes must have an identical coolant flow rate because they are connected to a same pump 2. As a result, independent control of the coolant flow rate, and thus the amount or rate of cooling, of more than two probes is impossible. Moreover, the existing cooled RF pump system 1 is incapable of determining which cooled RF ablation probe is connected to each respective one of the pumps 2 of the pump system 1. As a result, if an issue is encountered during a procedure in which the probe must be replaced, the clinician must trace electrical and fluid cables and/or tubes to their respective origins, i.e., RF channel and pump head, a cumbersome process which interrupts the procedure on the patient.

Consequently, a need currently exists for a cooled radiofrequency ablation pump system and method that can map active RF channels to their respective pump assemblies. In particular, a cooled radiofrequency ablation pump system and method that can further detect the presence of daisy-chained cooled radiofrequency probes connected in series to a single pump assembly would be useful.

SUMMARY

The present invention is directed to a method to map active radiofrequency channels to respective pump assemblies for cooled radiofrequency ablation. The method includes steps of: providing a pump system having a plurality of pump assemblies, a radiofrequency generator unit, and a plurality of cooled radiofrequency probes, wherein each cooled radiofrequency probe comprises a cable-tubing assembly having a radiofrequency cable and fluid tubing; connecting the cable of each cable-tubing assembly to an RF channel of the radiofrequency generator; connecting the fluid tubing of each cable-tubing assembly to a cooling fluid source; activating each pump assembly of the plurality of pump assemblies individually in sequence; and mapping each cooled radiofrequency probe to a respective pump assembly connected thereto using a temperature drop delay time, wherein the temperature drop delay time is the amount of time for cooling fluid to reach a tip of the cooled radiofrequency ablation probe and initiate a temperature decrease at the tip of the cooled radiofrequency ablation probe after activation of a first pump assembly of the plurality of pump assemblies.

In one particular embodiment, the step of activating each pump assembly of the plurality of pump assemblies individually in sequence can include activating each pump assembly individually in sequence with a pump activation time delay between the activation of each pump assembly. Further, the pump activation time delay can be from about 5 seconds to about 10 seconds.

In another embodiment, each radiofrequency probe can include a thermocouple at the tip of the probe configured to measure the temperature at the tip of the probe, the method further comprising a step of measuring the temperature at the tip of the probe. Moreover, the method can further include a step of measuring the temperature drop delay time between the time of activation of the first pump assembly and the time cooling fluid reaches the tip of the first radiofrequency ablation probe exhibiting a temperature decrease of at least 0.5 degrees.

In an additional embodiment, the step of mapping each cooled radiofrequency probe to a respective pump assembly connected thereto includes measuring the temperature drop delay for each cooled radiofrequency ablation probe and comparing the temperature drop delay time for each cooled radiofrequency ablation probe with the activation time of each of the pump assemblies. Further, each pump assembly can be mapped to the radiofrequency ablation probe that measures a temperature drop delay time soonest after the activation time of each pump assembly.

In yet another embodiment, the plurality of pump assemblies can include from two to four pump assemblies, further wherein the plurality of cooled radiofrequency probes can include from two to four cooled radiofrequency ablation probes.

In a further embodiment, the step of mapping each cooled radiofrequency probe to a respective pump assembly connected thereto further can include detecting the presence or absence of daisy-chained cooled radiofrequency probes, wherein daisy-chained cooled radiofrequency probes comprise two or more cooled radiofrequency probes associated with one pump assembly of the plurality of pump assemblies.

The present invention is further directed to a method of providing cooled radiofrequency ablation treatment to a patient. The method includes steps of: providing a pump system having a plurality of pump assemblies, a radiofrequency generator unit, and a plurality of cooled radiofrequency probes, wherein each cooled radiofrequency probe comprises a cable-tubing assembly having a radiofrequency cable and fluid tubing; connecting the cable of each cable-tubing assembly to an RF channel of the radiofrequency generator unit; connecting the fluid tubing of each cable-tubing assembly to a cooling fluid source; activating each pump assembly of the plurality of pump assemblies individually in sequence; mapping each cooled radiofrequency probe to a respective pump assembly connected thereto using a temperature drop delay time, wherein the temperature drop delay time is the amount of time for cooling fluid to reach a tip of the cooled radiofrequency ablation probe and initiate a temperature decrease at the tip of the cooled radiofrequency ablation probe after activation of a first pump assembly of the plurality of pump assemblies; inserting each cooled radiofrequency ablation probe into a target tissue area of the patient; and independently controlling each cooled radiofrequency probe to deliver cooled radiofrequency ablation treatment.

In one particular embodiment, the step of activating each pump assembly of the plurality of pump assemblies individually in sequence includes activating each pump assembly individually in sequence with a pump activation time delay between the activation of each pump assembly. Further, the pump activation time delay can be from about 5 seconds to about 10 seconds.

In another embodiment, each radiofrequency probe includes a thermocouple at the tip of the probe configured to measure the temperature at the tip of the probe, the method further comprising a step of measuring the temperature at the tip of the probe.

In an additional embodiment, the step of mapping each cooled radiofrequency probe to a respective pump assembly connected thereto further includes detecting the presence or absence of daisy-chained cooled radiofrequency probes, wherein daisy-chained cooled radiofrequency probes comprise two or more cooled radiofrequency probes associated with one pump assembly of the plurality of pump assemblies.

In one more embodiment, the step of independently controlling each cooled radiofrequency probe to deliver cooled radiofrequency ablation treatment includes independently controlling one or more of the respective pump assembly mapped to each cooled radiofrequency probe and the RF channel mapped to each cooled radiofrequency probe.

The present invention is further directed to a cooled radiofrequency ablation system. The system includes a pump system having a plurality of pump assemblies; a radiofrequency generator unit having a plurality of RF channels; and a plurality of cooled radiofrequency probes, wherein each cooled radiofrequency probe comprises a cable-tubing assembly having a radiofrequency cable and fluid tubing. The radiofrequency generator unit includes a controller having a memory device storing instructions which, when executed, cause the controller to: activate each of the pump assemblies individually in sequence with a pump activation time delay between the activation of each pump assembly; measure the pump activation time delay of each of the plurality of pump assemblies; measure the temperature drop delay time of each of the plurality of cooled radiofrequency ablation probes; compare the pump activation delay time of each of the plurality of pump assemblies with the temperature drop delay time of each of the cooled radiofrequency probes; and map each respective pump assembly to a corresponding cooled radiofrequency ablation probe based on the comparison.

In one embodiment, each radiofrequency probe includes a thermocouple at the tip of the probe configured to measure the temperature at the tip of the probe.

In another embodiment, the plurality of pump assemblies includes from two to four pump assemblies, further wherein the plurality of cooled radiofrequency probes comprises from two to four cooled radiofrequency ablation probes.

In a further embodiment, the plurality of cooled radiofrequency ablation probes includes at least two radiofrequency ablation probes daisy-chained to a single pump assembly.

In an additional embodiment, the memory device stores further instructions which, when executed, cause the controller to detect the presence of two or more cooled radiofrequency ablation probes daisy-chained to a single pump assembly.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
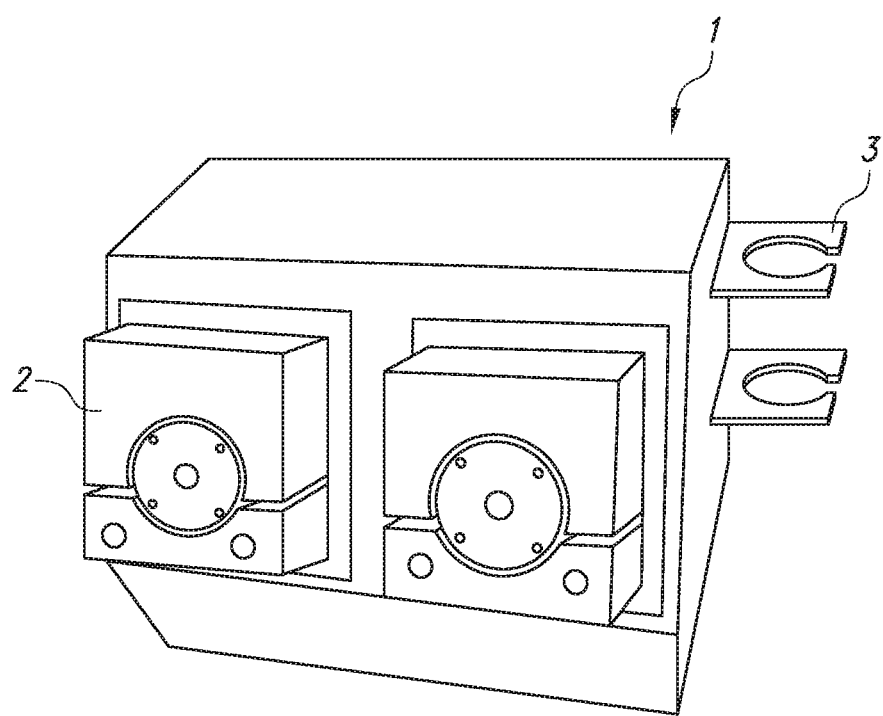
FIG. 1 illustrates a perspective view of a cooled RF pump system of the prior art.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

Generally speaking, the present invention is directed to a cooled radiofrequency ablation system and method, and in particular, a method to map active radiofrequency channels to respective pump assemblies for cooled radiofrequency ablation. The system includes a pump system having a plurality of pump assemblies, a radiofrequency generator unit, and a plurality of cooled radiofrequency probes, wherein each cooled radiofrequency probe comprises a cable-tubing assembly having a radiofrequency cable connected to the radiofrequency generator unit and a dual-lumen fluid tubing in communication with a pump assembly and connected to a cooling fluid source. Each pump assembly of the plurality of pump assemblies is activated individually in sequence. The system and method map each cooled radiofrequency probe to a respective pump assembly connected thereto by measuring a temperature drop delay time at the tip of each probe. The system and method can further detect the presence of multiple probes daisy-chained to a single pump assembly. The present inventor has found that the particular components of the radiofrequency ablation system and method of the present invention enable automated mapping between the plurality of pump assemblies and cooled radiofrequency ablation probes. Thus, the cooled radiofrequency ablation system can provide fully independent power control to each of the cooled radiofrequency ablation probes by independently controlling the individual pump assembly and RF channel associated with each probe. Moreover, the mapping generated by the present invention reduces the set-up time for the cooled radiofrequency ablation system prior to initiating a patient treatment procedure. In addition, if an issue is encountered during a cooled radiofrequency ablation procedure in which an individual probe must be replaced, the mapping of the present invention saves time in determining precisely which fluid conduit(s) and/or RF channel(s) are associated with the probe to be replaced. The specific features of the cooled radiofrequency ablation system and method of the present invention may be better understood with reference to FIGS. 1-8.

Figure 2A:
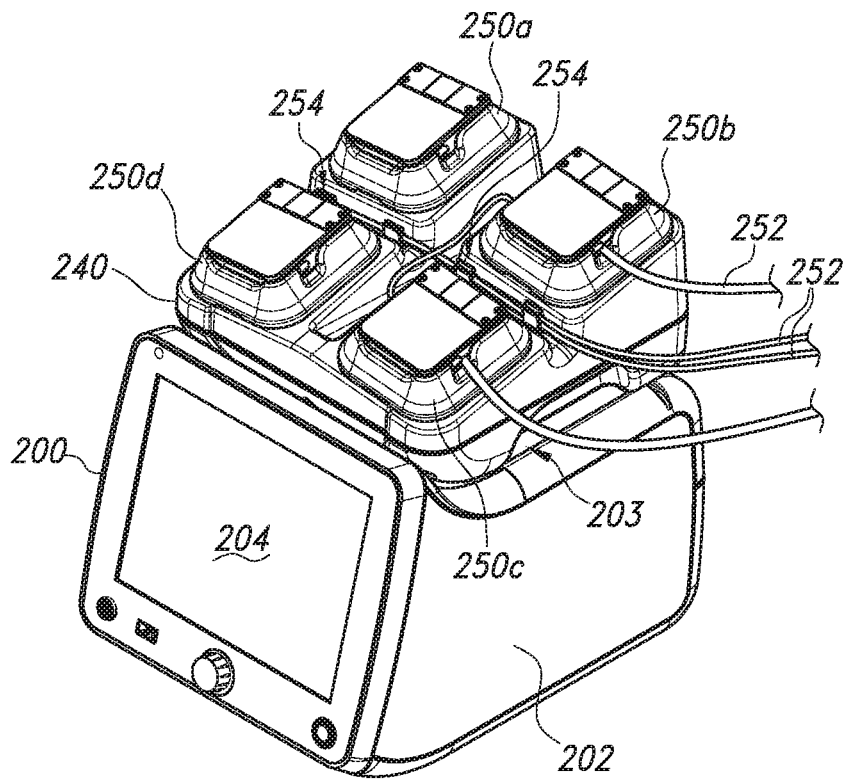
FIG. 2A illustrates a perspective view of a pump system and radiofrequency generator according to one particular embodiment of the present invention.
Figure 2B:
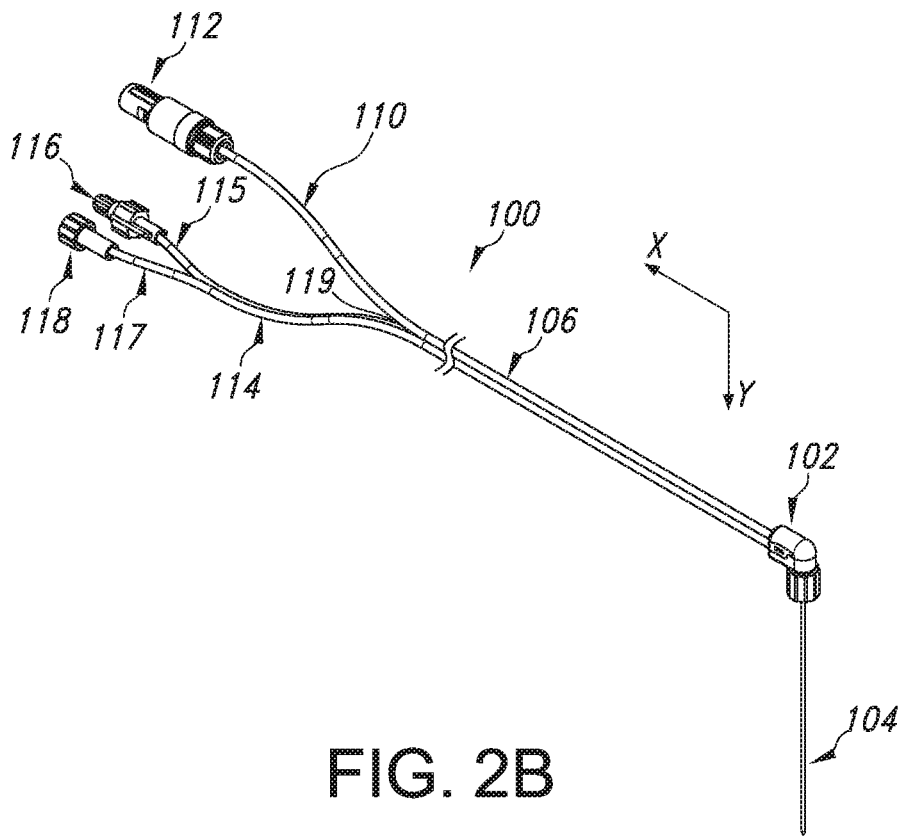
FIG. 2B illustrates a perspective view of a cooled radiofrequency ablation probe according to one particular embodiment of the present invention for use with the pump system and radiofrequency generator of FIG. 2A.

Referring now to the drawings, FIGS. 2A and 2B illustrate the components of one embodiment of the cooled radiofrequency ablation system 10 of the present invention. In particular, FIG. 2A illustrates a perspective view of a radiofrequency generator 200 and pump system 240 for the cooled radiofrequency ablation system 10 of the present invention. As shown, the generator 200 includes a housing 202 and a display 204, for example, a screen, a touch screen, or other graphic user interface. The generator housing 202 further includes a plurality of electrical connectors (not shown) through which the generator 200 is configured to be operably coupled to at least one radiofrequency ablation probe 100 to provide RF energy to the probe 100. The pump system 240 is configured to sit on the top surface 203 of the housing 202 of the generator 200. The pump system 240 includes a plurality, e.g., four (4), of peristaltic pump assemblies 250a, 250b, 250c and 250d. For ease of identification, the pump assemblies will be identified as first pump assembly 250a, second pump assembly 250b, third pump assembly 250c, and fourth pump assembly 250d. In some aspects of the invention, each of the pump assemblies 250a-d can be interchangeably removed from the pump system 240. The pump system 240 can further include tubes 252 configured to be associated with each respective pump assembly 250a-d such that the pump assemblies 250a-d each pump cooling fluid through the tubes 252. The tubes 252 can be held in place in the pump system 240 with clips 254 or any other suitable retaining means.

FIG. 2B illustrates an individual radiofrequency ablation probe 100 configured to be used with the pump system 240 and RF generator 200. The probe 100 includes a handle 102 and an elongate member 104 in the form of a shaft extending from one end of the handle 102. A cable-tubing assembly 106 extends from the opposite side of the handle 102 and includes an electrical cable 110 and a dual-lumen fluid tubing 114. The electrical cable 110 can include an insulating jacket 152 constructed from, for example, polyvinyl chloride (PVC) or any other suitable material. The electrical cable 110 can terminate at a proximal end at an electrical connector 112. The electrical connector 112 can be, for example, a circular electrical connector as shown in FIG. 2B. The dual-lumen fluid tubing 114 can be constructed from two lumens 115 and 117 having walls constructed from clear polyvinyl chloride (PVC). The walls of the two lumens 115 and 117 can be thermally bonded together. The dual-lumen fluid tubing 114 can terminate at a proximal end at Luer connector 116 of lumen 115 and Luer connector 118 of lumen 117. Luer connector 116 can be positioned at the proximal end of lumen 115 and Luer connector 118 can be positioned at the proximal end of lumen 117. For example, lumen 115 can be an inlet fluid lumen with Luer connector 116 functioning as an inlet fluid connector, and lumen 117 can be an outlet fluid lumen with Luer connector 118 functioning as an outlet fluid connector. In one embodiment, Luer connector 116 can be a male Luer connector and Luer connector 118 can be a female Luer connector. The cable-tubing assembly 106 can be bonded between an insulating jacket of the electrical cable 110 and the wall of at least one of the lumens of the dual-lumen fluid tubing 114 along the length of the assembly 106. The bonding can be done, for example, by heat welding, UV adhesive, or any other suitable form of welding or bonding plastic or polymeric materials together. For example, the electrical cable 110 can be disposed in a recess 119 between the walls of the two lumens 115 and 117, as illustrated in FIG. 2B. The cable-tubing assembly 106 can include at least one unbonded region on the proximal connector end of the cable-tubing assembly 106 in which the electrical cable 110 and the dual-lumen fluid tubing 114 are not bonded together such that the electrical cable 110 can be connected to the generator 200 and the dual-lumen fluid tubing 114 can be connected with tubing 252 of the pump system 240.

Figure 4:
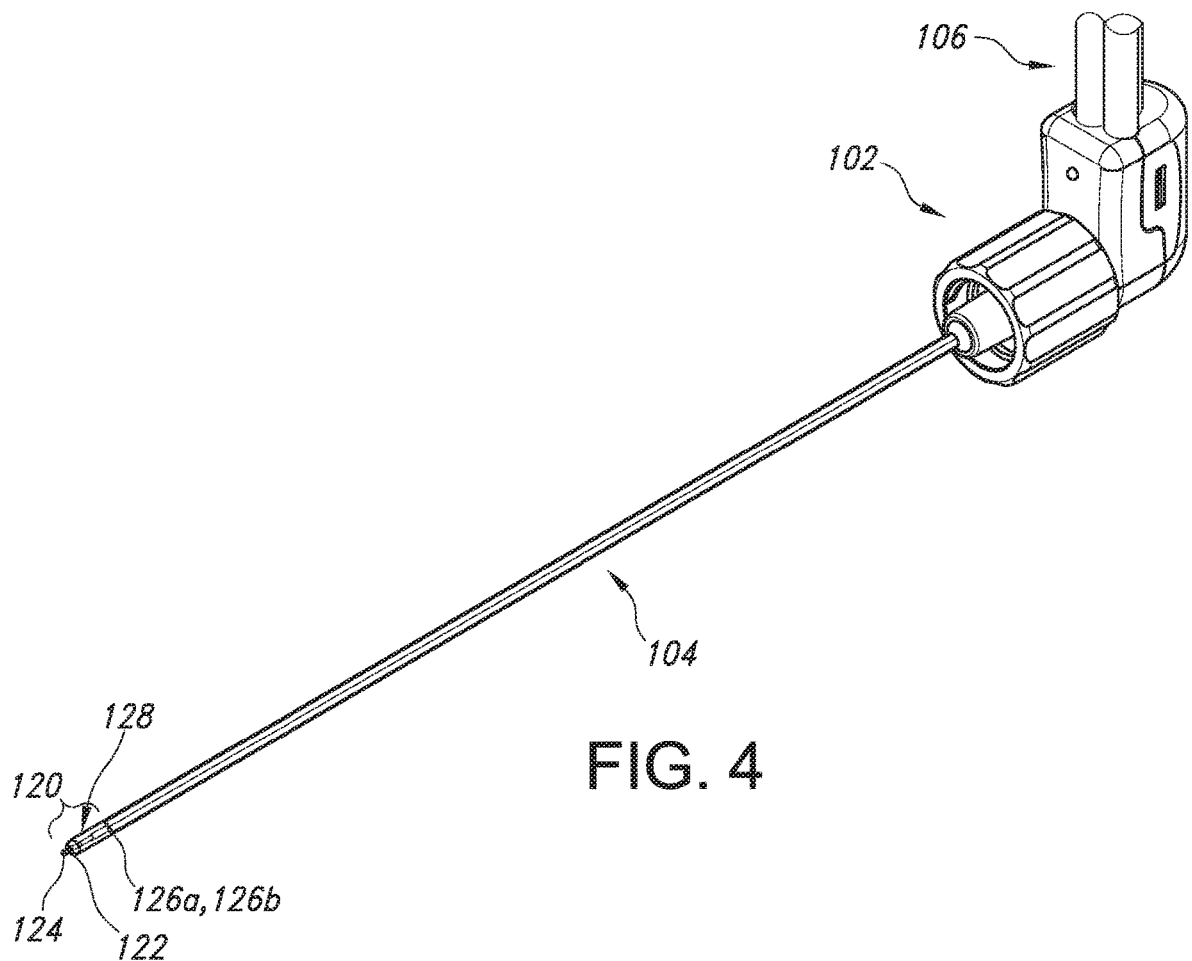
FIG. 4 illustrates a perspective view of a radiofrequency treatment assembly of the probe of FIG. 2B.
Figure 5:
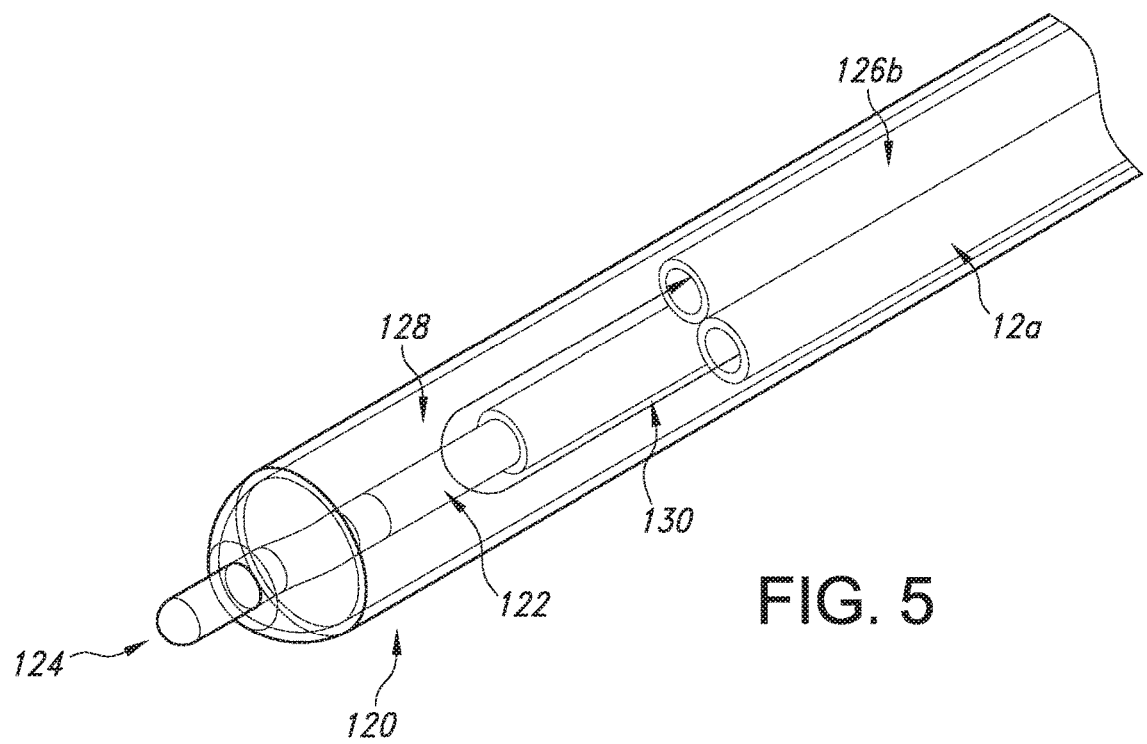
FIG. 5 illustrates a cut-away view of a distal end of the radiofrequency treatment assembly shown in FIG. 4.

FIGS. 4 and 5 illustrate details of the elongate member 104 of the probe 100. The elongate member 104 of each probe 100 forms an electrocap assembly that is thermally and electrically conductive for delivering electrical or radiofrequency energy to the patient's tissue. A distal end 120 of the elongate member 104 opposite the probe handle 106 forms an active tip 124 for delivering the cooled, radiofrequency treatment to the patient's tissue. The electrocap assembly may include at least one fluid conduit 126 within the elongate member 104, such as an inlet fluid conduit 126a and an outlet fluid conduit 126b, for delivering cooling fluid to and from the active tip 124. The electrocap assembly may additionally include a thermocouple hypotube 130 extending the length of the elongated member 104 and protruding from the distal end of the elongated member. The thermocouple hypotube 130 may include a wire 122 made from an electrically conductive material such as constant. The wire 122 can be insulated along the entire length of the elongate member 104 and welded to the hypotube 130 at a distal end 120 of the electrocap assembly to form a thermocouple 124. The cooling fluid may be circulated in a volume 128 within the distal end 120 of the electrocap assembly adjacent the thermocouple 124 to control the temperature of the active tip 124. Thus, RF energy can be transmitted to the active tip 124 via the wire 122, which generates thermal energy, and the cooling fluid circulating in the volume 128 from the inlet fluid conduit 126a to the outlet fluid conduit 126b can cool the active tip 124 to control the temperature increase at the active tip 124. Thus, the amount of tissue damage or ablation caused by RF energy delivered by the probe 100 in use can be modified by the circulation of cooling fluid through the elongate member 104.

Figure 3:
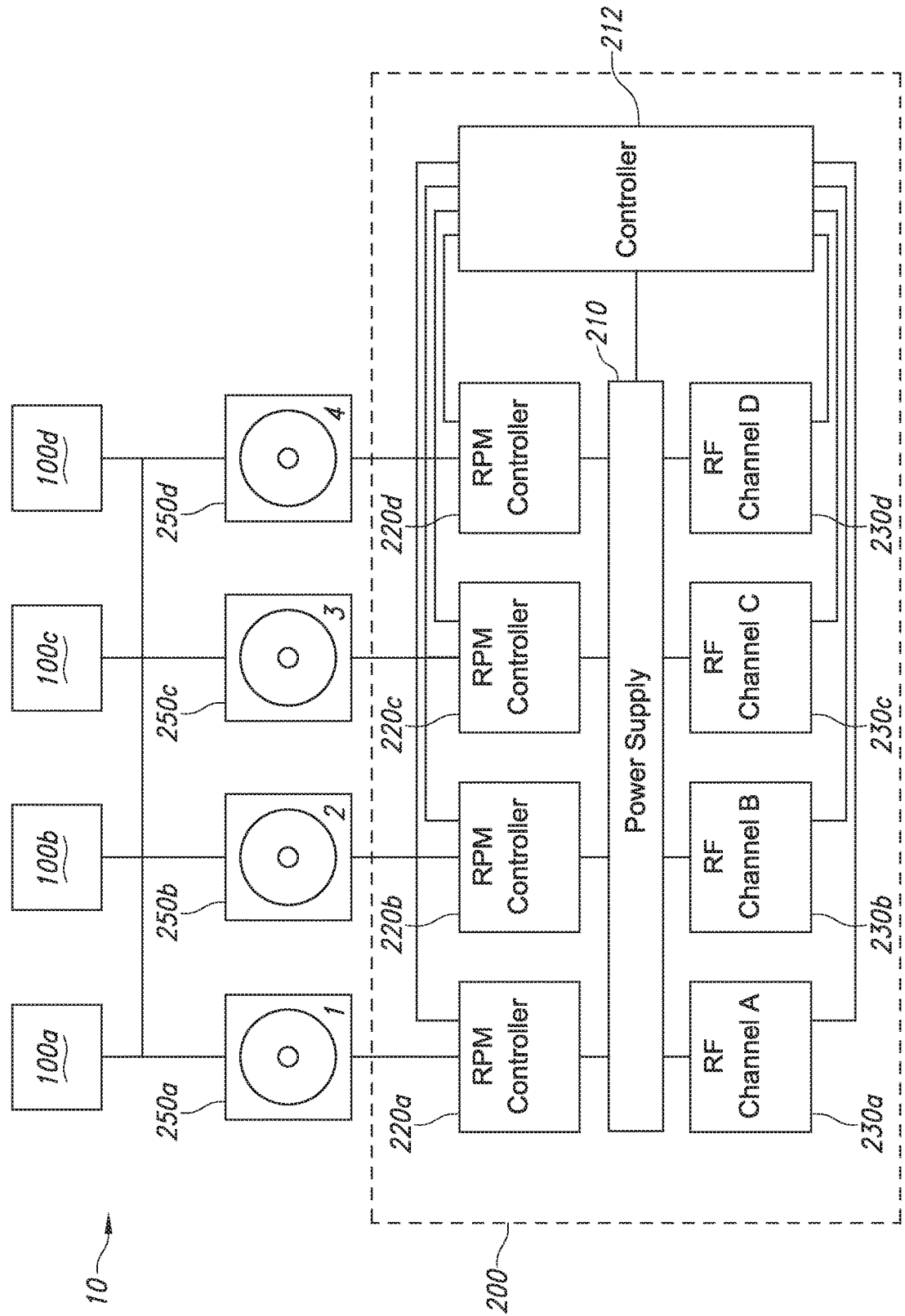
FIG. 3 illustrates a schematic block diagram of the cooled radiofrequency ablation system according to one particular embodiment of the present invention.

FIG. 3 shows a diagrammatic representation of the cooled radiofrequency ablation system 10 of the present invention, including pump system 240 having pumps 250a, 250b, 250c and 250d, controllers for the pumps 220a, 220b, 220c and 220d housed in the generator 200, and cooled radiofrequency treatment probes 100 for delivering treatment to patient tissue. The pump system 240, including a source of coolant fluid pumped through the tubing 252 to the probes 100a-d, works to reduce a temperature of material located at and proximate to one or more of the probe assemblies 100a-d. For example, as shown in FIG. 3, the pump system 240 may include a plurality of pump assemblies 250a-d each having a peristaltic pump (via pump rotors) operable to circulate a fluid from the pump system 240 through one or more proximal cooling supply tubes (e.g., tubing 252 of FIG. 2A), the probe assemblies 100a-d, one or more proximal cooling return tubes 252 (see FIG. 2A) and back to the coolant fluid source of the pump system 240. The peristaltic pump assemblies 250a-d are coupled to a power supply 210. The power supply 210 can be housed within or provided by the generator 200. In such embodiments, each of the plurality of pumps 250a-d may be in separate fluid communication with a respective one of the probe assemblies 100a-d. The fluid may be water, saline, or any other suitable fluid or gas. In alternate embodiments, the pump system 240 may include only one peristaltic pump or greater than four pumps. In addition, as shown in FIG. 3, each of the pumps 250a-d may have independent speed (i.e. rotations per minute or RPM) controllers 220a, 220b, 220c, and 220d that are configured to independently adjust the speed of each respective pump 250a-d.

FIG. 3 additionally shows a plurality of RF channels 230a, 230b, 230c and 230d within the generator 200. For ease of identification, the RF channels 230a-d will be identified as RF channel A 230a, RF channel B 230b, RF channel C 230c, and RF channel D 230d. The RF channels 230a-d are configured to be electrically connected with a respective one of the probes 100a-d to deliver RF energy to the probes 100a-d. For example, the electrical cable 110 (see FIG. 2B) of each respective probe 100a-d can be in operative communication with one of the RF channels 230a-d, e.g., by plugging in the electrical connector 112 into a respective one of the RF channel connections on the generator housing 202.

Still referring to FIG. 3, the system 10 may include a controller 212 for facilitating communication between the pump system 240 and the generator 200, including the RF channels 230a-d. In this way, feedback control is established between the pump system 240 and the RF channels 230a-d of the generator 200. The feedback control may include the generator 200, the probe assemblies 100a-d and the pump system 240, although any feedback between any two devices is within the scope of the present invention. The feedback control may be implemented, for example, in a controller or control module 212 which may be a component of the generator 200. In such embodiments, the generator 200 is operable to communicate bi-directionally with the probe assemblies 100a-d, e.g., via electrical connections (not shown) as well as with the pump system 240. In the context of this invention, bi-directional communication refers to the capability of a device to both receive a signal from and send a signal to another device. The controller 212 includes a processor, microprocessor, or any other computing device, optionally further including a memory device storing one or more control algorithms. The one or more control algorithms can include the feedback control between the pump system 240 and the generator 200, e.g., for independently controlling each of the probes 100a-d to deliver cooled RF ablation treatment.

However, as shown in FIGS. 2B and 3, the connections between each probe 100 and a respective pump assembly and RF channel are distinct. Stated another way, the cooling fluid tubing 114 of each probe 100 is separate from the electrical cable 112 of each probe 100, and so the probe 100 connected to first pump assembly 250a may not necessarily be connected to RF channel A 230a. Thus, it is necessary to map each RF channel to a respective pump assembly associated with each probe 100 in order to independently control each probe 100.

Figure 6:
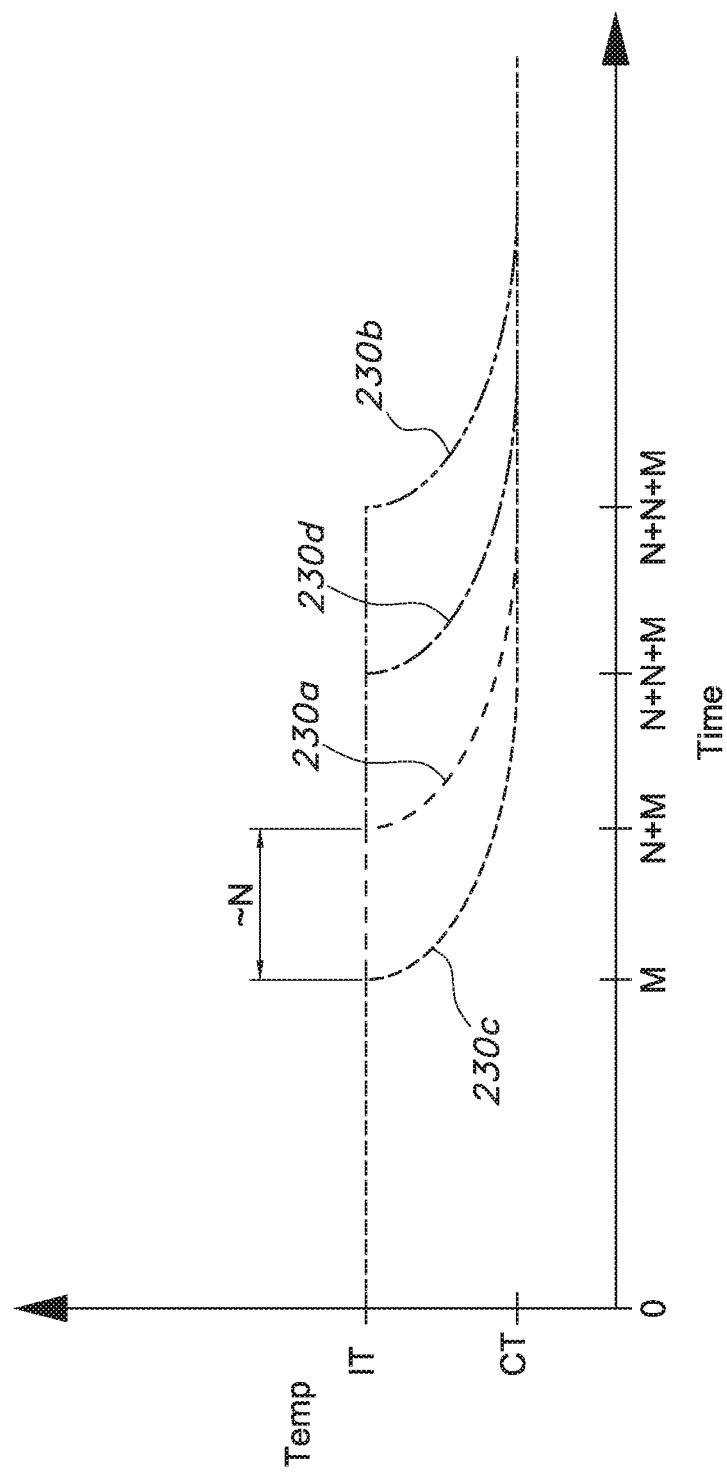
FIG. 6 illustrates a graph of temperature versus time of the sequential pump activation routine for mapping the pump assemblies to the RF channels of the system of FIG. 3.

The system 10 of the present invention uses a sequential pump activation routine to map each RF channel to a respective pump assembly associated with each probe 100. In particular, the sequential pump activation routine is implemented to prime the system 10, i.e., prime the cooling fluid tubes 252 and prepare the probes 100 for delivering cooled RF treatment, before activating any treatment of patient tissue using the cooled RF ablation probes 100. Each probe 100 is connected via its cable-tubing assembly 106 to the generator 200 via electrical connector 112 and to the cooling fluid tubing 252 via the inlet connector 116 and outlet connector 118. For example, each of the probes 100a-d as shown in FIG. 3 are connected to one of the pump assemblies 250a-d and one of the RF channels 230a-d. To prime the system 10, rather than initiating all of the pump assemblies 250a-d simultaneously, each of the pump assemblies 250a-d are activated individually in a predetermined sequence. For instance, first pump assembly 250a is activated first, second pump assembly 250b is activated second, third pump assembly 250c is activated third, and fourth pump assembly 250d is activated last. The predetermined sequence includes a pump activation time delay N. The pump activation time delay N is equal in between activation of each of the respective pump assemblies 250a-d. For instance, first pump assembly 250a is activated at time T=0 seconds, second pump assembly 250b is activated at time T=N seconds, third pump assembly 250c is activated at time T=N+N seconds (stated alternatively, T=2*N seconds), and fourth pump assembly 250d is activated at time T=N+N+N seconds (stated alternatively, T=3*N seconds), as illustrated in FIG. 6. The pump activation time delay can be from about 5 seconds to about 10 seconds, or any value therebetween.

As the pump assemblies 250a-d are activated in the predetermined sequence as described above, cooling fluid is transported through the tubing 252, inlet fluid lumen 115 of the cable-tubing assembly 106 and the inlet fluid conduit 126a of each respective one of the probes 100a-d to the active tip 124 of the elongate member 104 of each of the respective probes 100a-d. When the cooling fluid reaches the thermocouple of the active tip 124, a temperature drop is registered by the thermocouple 124. For instance, the temperature at the active tip 124 of each of the respective probes 100a-d drops from an initial temperature IT to a cooled temperature CT. Each of the probes 100a-d has a temperature drop delay M. The temperature drop delay M is equal to the amount of time that passes between the initiation of a respective pump assembly and the time that the cooling fluid reaches the thermocouple of the active tip 124 of the probe 100 associated with the respective pump assembly to register a temperature drop of at least 0.5 degrees Celsius, such as from 0.5 degrees Celsius to about 10 degrees Celsius. In some particular embodiments, the temperature drop can be in a range from about 1 degree Celsius to about 5 degrees Celsius, such as from about 2 degrees Celsius to about 4 degrees Celsius, e.g., about 3 degrees Celsius. The temperature at the active tip 124 then cools from the initial temperature IT to the desired cooled temperature CT after the cooling fluid reached the active tip 124. Assuming that the volumetric flow rate, path length of the tubing 252 and cross-sectional area of tubing 252 associated with each of the respective probes 100a-d and pump assemblies 250a-d are equal for all four probes 100a-d, the time it takes for the cooling fluid to reach the active tip 124 of each of the probes 100a-d, i.e., the temperature drop delay M, is equal.

In order to map the respective RF channels 230a-d to each of the pump assemblies 250a-d associated with each of the probes 100a-d, the above described sequential pump activation routine is implemented. For the sake of simplicity, it will be assumed that the probe 100a is electrically connected to RF channel A 230a, probe 100b is electrically connected to RF channel B 230b, probe 100c is electrically connected to RF channel C 230c, and probe 100d is electrically connected to RF channel D 230d. The pump assemblies 250a-d are activated individually in sequence with the pump activation time delay N between activation of each respective pump assembly, for example, in the order of first pump assembly 250a at time T=0, second pump assembly 250b at time T=N, third pump assembly 250c at time T=N+N, then fourth pump assembly 250d and time T=N+N+N. The generator 200 receives information from the active tip thermocouple 124 of each of the respective probes 100a-d via the respective RF channels 230a-d and records the time at which the active tip thermocouple 124 of each of the probes 100a-d registers a temperature drop M. The controller 212 compares the temperature drop delay, i.e., the time at which the active tip thermocouple 124 of each of the probes 100a-d registers a temperature drop, with the known sequence of activation of the pump assemblies 250a-d. The probe 100a-d associated with the RF channel 230a-d that has a total temperature drop delay soonest after each one of the respective pump assemblies 250a-d is activated is then mapped to that pump assembly. As shown in FIG. 6, RF channel C 230c (associated with probe 100c) registered a temperature drop to the cooled temperature CT soonest after the first pump assembly 250a was activated, thus RF channel C 230c (and associated probe 100c) is mapped to the first pump assembly 250a. Next, RF channel A 230a (associated with probe 100a) registered a temperature drop to the cooled temperature CT, thus RF channel A 230a is mapped to the second pump assembly 250b. The RF channel D 250d (and associated probe 100d) next registered a temperature drop to the cooled temperature CT, so RF channel D 230d is mapped to the third pump assembly 250c. Finally, RF channel B 230b (and associated probe 100b) registered a temperature drop to the cooled temperature CT last, so RF channel B 230b is mapped to the fourth pump assembly 250d.

The controller 212 may further confirm the mapping of the RF channels to the pump assemblies by calculating the actual temperature drop delay times measured by each RF channel and comparing them to the theoretical temperature drop delay time based on the known values of pump activation time delay N and temperature drop delay M, where M is the time it takes the cooling fluid to reach the active tip 124 as evidenced by a decrease in the active tip temperature measured by the thermocouple. For instance, the temperature drop delay of RF channel C 230c (probe 100c) mapped to the first pump assembly 250a should be equal to M, as first pump assembly 250a has no pump activation time delay (because first pump assembly 250a is activated at time T=0). The temperature drop delay of RF channel A 230a (probe 100a) mapped to the second pump assembly 250b should be equal to N+M, as second pump assembly 250b has a pump activation time delay equal to N. The temperature drop delay of RF channel D 230d (probe 100d) mapped to the third pump assembly 250c should be equal to N+N+M, as third pump assembly 250c has a pump activation time delay equal to N+N. The temperature drop delay of RF channel B 230b (probe 100b) mapped to the fourth pump assembly 250d should be equal to N+N+N+M, as fourth pump assembly 250d has a pump activation time delay equal to N+N+N.

As shown in FIG. 6, the time and temperature measurements of each of the RF channels 230a-d during the sequential pump activation routine can be graphically represented on the display 204. The graphical representation can be in the form of a temperature versus time graph, shown in FIG. 6, or any other suitable graphic or image displayed to indicate the mapping of the RF channels 230a-d to the pump assemblies 250a-d. Thus, the clinician(s) administering the cooled RF ablation treatment will be able to see which pump assemblies 250a-d are associated with which RF channels 230a-d to be able to independently control each of the probes 100a-d. Moreover, if an issue is encountered during the cooled RF ablation treatment and a probe needs to be replaced, the graphic on the display 204 will make it easy for the clinician to determine which pump assembly and which RF channel are associated with the affected probe.

Figure 7:
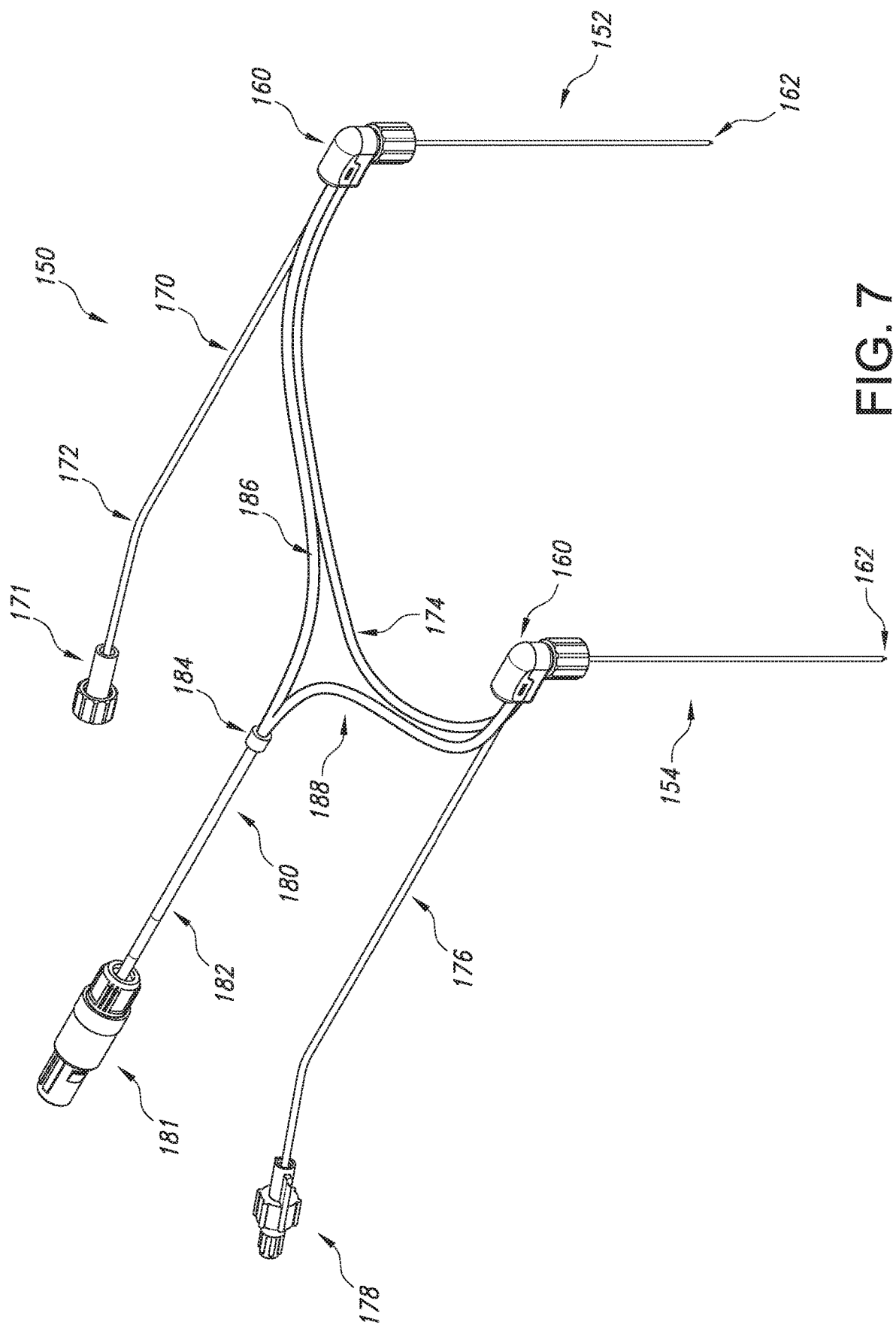
FIG. 7 illustrates a daisy-chained probe assembly according to another particular embodiment of the present invention.

As shown in FIG. 7, in some aspects of the invention, a daisy-chained probe assembly 150 includes two probes 152 and 154 daisy-chained together, i.e., arranged in series, with the second probe 154 being positioned downstream of the first probe 152. In an alternate embodiment, the probe assembly can include more than two probes. The probe assembly 150 further includes an electrical cable 180 for supplying energy to the probes 152 and 154, and cooling fluid tubing 170 for carrying cooling fluid to and from the probes 152 and 154. The electrical cable 180 and the cooling fluid tubing 170 communicate with each of the probes 152, 154 at a probe handle 160 of each probe.

The electrical cable 180 may be formed as a Y-shaped electrical cable. Alternately, the electrical cable 180 may be T-shaped. The electrical cable 180 includes an electrical connector 181 located at an end of the cable 180 opposite from the probes 152, 154. The connector 181 is connected to a single electrical cable 182. The single electrical cable 182 splits at a grommet 184 into two discrete cables with three conductors each, forming a first probe electrical cable 186 which connects to the first probe 152 and a second probe electrical cable 188 which connects to the second probe 154. As shown in FIG. 7, the probes 152, 154 can be connected to the electrical cable 180 in parallel via the first probe electrical cable 186 and the second probe electrical cable 188.

Still referring to FIG. 7, the cooling fluid tubing 170 can include an inlet connector 171, for example a female Luer connector, for connecting to a cooling fluid source (not shown). The cooling fluid tubing 170 inlet portion 172 may extend from the inlet connector 171 to the first probe 152. A connecting tubing portion 174 of cooling fluid tubing 170 extends between the first probe 152 and the second probe 154, which is downstream of the first probe 152 along the fluid tubing 170. An outlet tubing portion 176 can extend from the second probe 154 to an outlet connector 178, for example a male Luer connector. In one embodiment, the outlet connector 178 may connect to the cooling fluid source (not shown) to form a closed-loop cooling fluid system. In an alternative embodiment, the outlet connector 178 may connect to a waste bag (not shown) for disposal of the cooling fluid.

The connecting tubing portion 174 can connect between the first probe 152 and the second probe 154 so that cooling fluid flows from the first probe 152 to the second probe 154 before flowing through outlet tubing portion 176 to the fluid source or waste bag (not shown). The connecting tubing portion 174 may cool the cooling fluid based on the temperature of ambient air. For example, if cooling fluid is heated as it flows through the first probe 152, the heat captured by the cooling fluid can be dissipated into the atmosphere by the ambient air temperature as the cooling fluid flows through connecting tubing portion 174 before reaching the second probe 154. The connecting tubing portion 174 can have a length sufficient to dissipate any heat captured by cooling fluid in the first probe into the atmosphere prior the cooling fluid flowing into the second probe 154. However, the path length for cooling fluid to reach the active tip of the first probe 152 is unequal to the path length for cooling fluid to reach the active tip of the second probe 154 because cooling fluid must pass through the first probe 152 and the connecting tubing portion 174 to reach the active tip of the second probe 154. Thus, the temperature drop delay of the second probe 154 will differ from any of the known pump activation delay times (i.e., 0, N, N+N, N+N+N) or temperature drop delay times (i.e., 0+M, N+M, N+N+M, N+N+N+M) because a single cooling fluid tubing 170 is used for both probes 152 and 154. Moreover, although probes 152 and 154 are electrically connected in parallel and receive RF energy at the same time, the temperature drop delay will differ for probes 152 and 154 due to the additional delay in receiving cooling fluid at the active tip of the second probe 154.

Thus, the sequential pump activation routine of the present invention can be used to determine whether there are daisy-chained probes associated with any of the RF channels 230a-d and/or pump assemblies 250a-d. Because the pump activation time delays are known (i.e., 0, N, N+N, N+N+N) and the cooling time delay M of individual (i.e., non daisy-chained) probes 100a-d is known, the controller 212 can compare the temperature drop delay of each RF channel to determine if the temperature drop delay does not match any of the known values in sequence following the activation of one or more of the pump assemblies 250a-d. For instance, when probes 152 and 154 are daisy-chained together, probe 154 will register a temperature drop delay slightly longer than the temperature drop delay of the probe 152 after its associated pump assembly is activated, but may be before or after any subsequent pump assembly is activated and unequal to any known temperature drop delay times (i.e., 0+M, N+M, N+N+M, N+N+N+M), thus indicating to the controller 212 that the probes 152 and 154 are daisy-chained together.

After the sequential pump activation routine is performed, the system 10 is prepared and ready to deliver cooled RF ablation treatment to patient tissue. A clinician, e.g., a surgeon, inserts the probes 100a-d into the patient's tissue if they have not already done so, such that the probes 100a-d each target one or more specific nerves. Then, using the mapping between the RF channels 230a-d connected to the probes 100a-d and the pump assemblies 250a-d, each of the probes 100a-d may be independently controlled to deliver cooled RF ablation treatment. For instance, the pump assembly associated with each respective one of the probes 100a-d can be controlled to have different volumetric flow rates of cooling fluid, thereby altering the degree of cooling in the active tip 124 of each of the probes 100a-d. Similarly, the generator 200 can independently control the amount of RF energy delivered through each of the RF channels 230a-d to the probes 100a-d.

Figure 8:
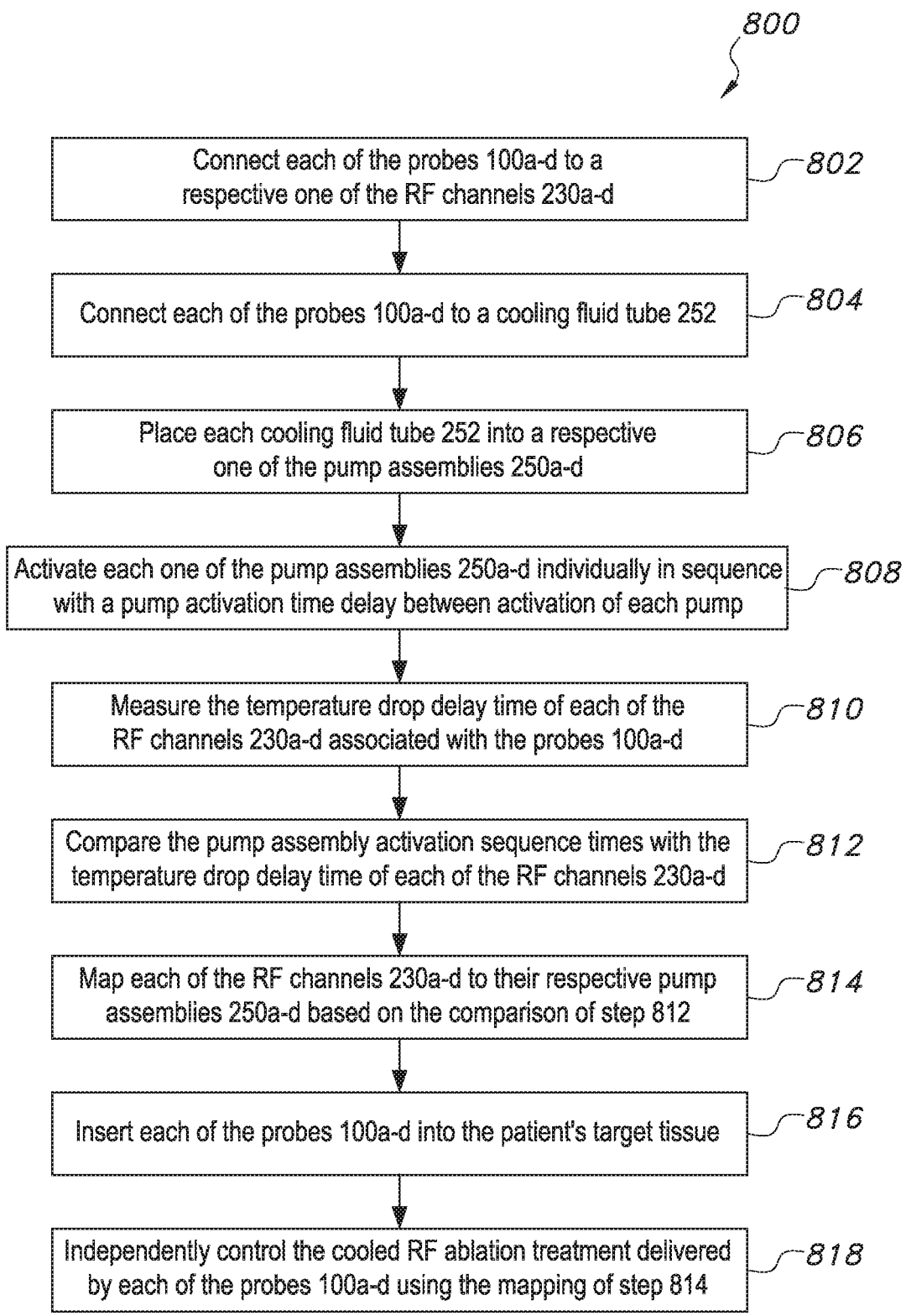
FIG. 8 illustrates a method of providing cooled radiofrequency ablation treatment according to one embodiment of the present invention.

The present invention is further directed to a method 800 of cooled RF ablation treatment including the sequential pump activation routine, as shown in FIG. 8. In step 802, each of the probes 100a-d are connected to a respective one of the RF channels 230a-d using the electrical cable 110 and electrical connector 112 of the cable-tubing assembly 106 of each respective probe. In step 804, each of the probes 100a-d are connected to a cooling fluid tube 252, e.g., via the inlet fluid connector 116 of the fluid lumen 115 of the cable-tubing assembly 106 of each respective probe. Then, in step 806, each cooling fluid tube 252 is inserted into a respective one of the pump assemblies 250a-d.

Next, the sequential pump activation routine is performed. In step 808, each one of the pump assemblies 250a-d is activated individually in sequence, with an activation time delay N between the activation of each pump assembly. The temperature drop time delay of each of the RF channels 230a-d is measured in step 810, where the temperature drop delay time is the time it takes for cooling fluid to reach the active tip as evidenced by a temperature drop measured by the thermocouple at the active tip. Then, in step 812, the temperature drop time delay of each of the RF channels 230*a-d* is compared with the known pump assembly activation times. Using the comparison of step 812, in step 814, each of the RF channels 230*a-d* are mapped to their respective pump assemblies 250*a-d* based on which RF channel registered a temperature drop delay time soonest after the activation time of each respective one of the pump assemblies 250*a-d*. The mapping of the RF channels 230*a-d* and pump assemblies 250*a-d* is then displayed on the display 204, e.g., as a graph.

After the sequential pump activation routine has been performed and the probes 100*a-d* have been mapped with their RF channels 230*a-d* and pump assemblies 250*a-d*, the system 10 is ready to deliver cooled RF ablation treatment to a patient. In step 816, each of the probes 100*a-d* is inserted into the patient's target tissue for treatment. Then, in step 818, each of the probes 100*a-d* are independently controlled by the generator 200 to deliver cooled RF ablation treatment by using the mapping generated in step 814 to individually control each one of the RF channels 230*a-d* and the pump assemblies 250*a-d*.

It should be understood that, although the embodiment illustrated in FIGS. 2A and 3 illustrate a system 10 having four pump assemblies 250*a-d*, RF channels 230*a-d* and probes 100*a-d*, respectively, the present invention contemplates any number of pump assemblies, RF channels and probes for cooled RF ablation treatment. In particular, the present invention can include two or more pump assemblies, RF channels and probes for cooled RF ablation treatment. Moreover, as demonstrated by the daisy-chained probes 152 and 154 illustrated in FIG. 6 and described above, the present invention contemplates implementing multiple treatment probes per individual pump assembly and/or RF channel.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A method to map active radiofrequency channels to respective pump assemblies for cooled radiofrequency ablation, the method comprising steps of:
   providing a pump system having a plurality of pump assemblies, a radiofrequency generator unit, and a plurality of cooled radiofrequency probes, wherein each cooled radiofrequency probe comprises a cable-tubing assembly having a radiofrequency cable and fluid tubing;
   connecting the cable of each cable-tubing assembly to an RF channel of the radiofrequency generator;
   connecting the fluid tubing of each cable-tubing assembly to a cooling fluid source;
   activating each pump assembly of the plurality of pump assemblies individually in sequence;
   mapping each cooled radiofrequency probe to a respective pump assembly connected thereto by measuring a temperature drop delay time for each cooled radiofrequency probe, wherein the temperature drop delay time is the amount of time for cooling fluid to reach a tip of the cooled radiofrequency ablation probe and initiate a temperature decrease at the tip of the cooled radiofrequency ablation probe after activation of a first pump assembly of the plurality of pump assemblies; and
   confirming the mapping of each cooled radiofrequency probe to the respective pump assembly by comparing the measured temperature drop delay time to an expected temperature drop delay time for each cooled radiofrequency probe, wherein expected temperature drop delay time is calculated using a recorded activation time of each cooled radiofrequency probe.

2. The method of claim 1, wherein the step of activating each pump assembly of the plurality of pump assemblies individually in sequence comprises activating each pump assembly individually in sequence with a pump activation time delay between the activation of each pump assembly.

3. The method of claim 2, wherein the pump activation time delay is from about 5 seconds to about 10 seconds.

4. The method of claim 1, wherein each radiofrequency probe comprises a thermocouple at the tip of the probe configured to measure the temperature at the tip of the probe, the method further comprising a step of measuring the temperature at the tip of the probe.

5. The method of claim 4, wherein the temperature drop delay time is measured between the time of activation of the first pump assembly and the time cooling fluid reaches the tip of the first radiofrequency ablation probe exhibiting a temperature decrease of at least 0.5 degrees Celsius.

6. The method of claim 1, wherein each pump assembly is mapped to the radiofrequency ablation probe that measures the temperature drop delay time soonest after the recorded activation time of each pump assembly.

7. The method of claim 1, wherein the plurality of pump assemblies comprises from two to four pump assemblies, further wherein the plurality of cooled radiofrequency probes comprises from two to four cooled radiofrequency ablation probes.

8. The method of claim 1, wherein the step of mapping each cooled radiofrequency probe to a respective pump assembly connected thereto further comprises detecting the presence or absence of daisy-chained cooled radiofrequency probes, wherein daisy-chained cooled radiofrequency probes comprise two or more cooled radiofrequency probes associated with one pump assembly of the plurality of pump assemblies.

9. A method of providing cooled radiofrequency ablation treatment to a patient, the method comprising steps of:
   providing a pump system having a plurality of pump assemblies, a radiofrequency generator unit, and a plurality of cooled radiofrequency probes, wherein each cooled radiofrequency probe comprises a cable-tubing assembly having a radiofrequency cable and fluid tubing;
   connecting the cable of each cable-tubing assembly to an RF channel of the radiofrequency generator unit;
   connecting the fluid tubing of each cable-tubing assembly to a cooling fluid source;
   activating each pump assembly of the plurality of pump assemblies individually in sequence;
   mapping each cooled radiofrequency probe to a respective pump assembly connected thereto by measuring a temperature drop delay time for each cooled radio frequency probe, wherein the temperature drop delay time is the amount of time for cooling fluid to reach a tip of the cooled radiofrequency ablation probe and initiate a temperature decrease at the tip of the cooled radiofrequency ablation probe after activation of a first pump assembly of the plurality of pump assemblies;

confirming the mapping of each cooled radiofrequency probe to the respective pump assembly by comparing the measured temperature drop delay time to an expected temperature drop delay time for each cooled radiofrequency probe, wherein expected temperature drop delay time is calculated using a recorded activation time and of each cooled radiofrequency probe;

inserting each cooled radiofrequency ablation probe into a target tissue area of the patient; and independently controlling each cooled radiofrequency probe to deliver cooled radiofrequency ablation treatment.

10. The method of claim 9, wherein the step of activating each pump assembly of the plurality of pump assemblies individually in sequence comprises activating each pump assembly individually in sequence with a pump activation time delay between the activation of each pump assembly.

11. The method of claim 10, wherein the pump activation time delay is from about 5 seconds to about 10 seconds.

12. The method of claim 9, wherein each radiofrequency probe comprises a thermocouple at the tip of the probe configured to measure the temperature at the tip of the probe, the method further comprising a step of measuring the temperature at the tip of the probe.

13. The method of claim 9, wherein the step of mapping each cooled radiofrequency probe to a respective pump assembly connected thereto further comprises detecting the presence or absence of daisy-chained cooled radiofrequency probes, wherein daisy-chained cooled radiofrequency probes comprise two or more cooled radiofrequency probes associated with one pump assembly of the plurality of pump assemblies.

14. The method of claim 9, wherein the step of independently controlling each cooled radiofrequency probe to deliver cooled radiofrequency ablation treatment comprises independently controlling one or more of the respective pump assembly mapped to each cooled radiofrequency probe and the RF channel mapped to each cooled radiofrequency probe.

15. A cooled radiofrequency ablation system comprising: a pump system having a plurality of pump assemblies;

a radiofrequency generator unit having a plurality of RF channels; and a plurality of cooled radiofrequency probes, wherein each cooled radiofrequency probe comprises a cable-tubing assembly having a radiofrequency cable and fluid tubing;

wherein the radiofrequency generator unit comprises a controller having a memory device storing instructions which, when executed, cause the controller to:
(i) activate each of the pump assemblies individually in sequence with a pump activation time delay between the activation of each pump assembly;
(ii) measure the pump activation time delay of each of the plurality of pump assemblies;
(iii) measure the temperature drop delay time of each of the plurality of cooled radiofrequency ablation probes;
(iv) compare the pump activation delay time of each of the plurality of pump assemblies with the temperature drop delay time of each of the cooled radiofrequency probes;
(v) map each respective pump assembly to a corresponding cooled radiofrequency ablation probe based on the comparison; and
(vi) confirm the mapping of each respective pump assembly to the corresponding cooled radiofrequency ablation probe by comparing the measured temperature drop delay time to an expected temperature drop delay time for each cooled radiofrequency probe, wherein expected temperature drop delay time is calculated using a recorded activation time of each cooled radiofrequency probe.

16. The cooled radiofrequency ablation system of claim 15, wherein each radiofrequency probe comprises a thermocouple at the tip of the probe configured to measure the temperature at the tip of the probe.

17. The cooled radiofrequency ablation system of claim 15, wherein the plurality of pump assemblies comprises from two to four pump assemblies, further wherein the plurality of cooled radiofrequency probes comprises from two to four cooled radiofrequency ablation probes.

18. The cooled radiofrequency ablation system of claim 15, wherein the plurality of cooled radiofrequency ablation probes comprises at least two radiofrequency ablation probes daisy-chained to a single pump assembly.

19. The cooled radiofrequency ablation system of claim 15, wherein the memory device stores further instructions which, when executed, cause the controller to detect the presence of two or more cooled radiofrequency ablation probes daisy-chained to a single pump assembly.

* * * * *